United States Patent [19]

Carlock

[11] 4,178,312
[45] Dec. 11, 1979

[54] IRIDIUM OR RHODIUM CATALYSTS FOR HYDROFORMYLATION AND ISOMERIZATION OF OLEFINS

[75] Inventor: John T. Carlock, Ponca City, Okla.

[73] Assignee: Conoco, Inc., Ponca City, Okla.

[21] Appl. No.: 924,603

[22] Filed: Jul. 14, 1978

[51] Int. Cl.$^2$ ............................................. C07C 45/08
[52] U.S. Cl. ............................................. 260/604 HF
[58] Field of Search ................ 260/604 HF; 568/909

[56] References Cited

U.S. PATENT DOCUMENTS

| | | | |
|---|---|---|---|
| 3,378,590 | 4/1968 | Usami et al. | 568/909 |
| 3,636,159 | 1/1972 | Solomon | 568/604 HF |
| 3,652,676 | 3/1972 | Kahle et al. | 568/604 HF |
| 3,752,859 | 8/1973 | Schell | 568/604 HF |
| 4,066,705 | 1/1978 | Hughes | 568/604 HF |

Primary Examiner—Werren B. Lone
Attorney, Agent, or Firm—Cortlan R. Schupbach, Jr.

[57] ABSTRACT

A catalyst of the general structure

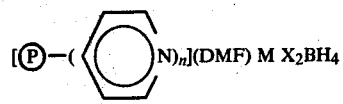

is an effective hydroformylation catalyst at temperatures of from about 60° to about 150° C. and hydrogen carbon monoxide gas pressures of from about 300 to about 3500 psig for both primary and internal olefins producing an increased amount of linear normal aldehydes through olefin isomerization. When the reactor gas is altered to essentially pure hydrogen, the catalyst further converts aldehydes formed by hydroformylation to alcohols under the same reaction conditions. The catalyst is air insensitive, stable, and highly recoverable by simple means. Ⓟ is a heterocyclic nitrogen-containing polymer with available pyridine linkages and n is 1 or 2.

7 Claims, No Drawings

IRIDIUM OR RHODIUM CATALYSTS FOR HYDROFORMYLATION AND ISOMERIZATION OF OLEFINS

The instant invention relates to an air stable rhodium and iridium-containing catalysts. More particularly, the instant invention relates to air stable rhodium and iridium dimethylformamide dihaloborohydride catalysts for hydroformylation and olefin isomerization reaction.

The hydroformylation of terminal (or alpha) olefins by certain homogeneous rhodium catalysts is known in the art. Representative examples of references describing rhodium catalysts used in hydroformylation reactions and reaction conditions necessary are found in U.S. Pat. Nos. 3,917,661; 3,907,847; 3,821,311; 3,499,932; 3,527,809; 3,825,601; 3,948,999; and 3,984,478. Literature references teaching polymer-bound catalysts include Tetrahedron Letters, 1971 (50) 4787-90, Grubbs et al, Journal of Macrmol. Sci. Chem., 1972, 13 (12), 828-32. While these references are not exhaustive of the art, they appear to be representative of hydroformylation in the current state of the art. However, these catalysts and reactions are generally very poor when used with internal olefins while the catalysts are dissolved in the reaction mixture, said catalysts being difficult to recover. In addition, these materials usually employ Group V ligands such as phosphines, phosphites, organo-arsines, and organo-antimony compounds which are very toxic and are air sensitive. Recovery of the catalyst is important since rhodium is an extremely expensive metal and the product cost rises sharply with each percentage drop in rhodium recovery from a previous reaction.

Hydroformylation is a reaction which converts olefins equivalent to alkenes for the purpose of this specification and claims to aldehydes such as shown in the formula below:

wherein R is hydrogen or an alkyl. Usually the hydroformylation procedure is followed by the hydrogenation of aldehydes to produce alcohol. However, the hydrogenation procedure is relatively simple and can be carried out by any one of several well-known means. In this procedure of converting olefins to alcohols the most difficult and least efficient step is the initial hydroformylation conversion of olefins to aldehydes. In the art cited above, such conversions have been accomplished, but only using catalysts which are difficult to recover and in some cases are extremely toxic.

U.S. Pat. Nos. 3,636,159 and 3,652,670 teach rhodium containing catalysts bound to polymers. However, these materials contain carbonyl groups and are not shown to be useful for hydrogenation. These catalysts are likewise not shown to be useful for the isomerization of internal olefins to primary olefins or for the subsequent hydroformylation of these materials to aldehydes.

It would therefore be of great benefit to provide a catalyst which has high levels of activity for the conversions of olefins to aldehydes (hydroformylation or oxo reactions), is easily prepared, readily recovered, and has a lack of sensitivity to oxygen.

It is therefore an object of the present invention to provide a method and a catalyst for hydroformylation, isomerization, and hydrogenation reactions, said catalyst being air stable, recoverable, and reuseable. Other objects will become apparent to those skilled in this art as the description proceeds.

It has now been discovered according to the present invention that olefins can be converted to aldehydes in the presence of a catalyst of the formula

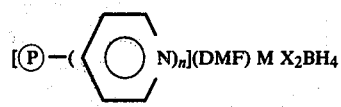

said conversions being carried out at temperatures of from about 60° C. to about 150° C. and hydrogen carbon monoxide pressures of from about 300 to about 3500 psig, wherein

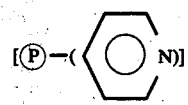

is a heterocyclic nitrogen-containing polymer with available pyridine linkages, M is rhodium or iridium, n is 1 or 2, and X is selected from the group consisting of bromine, chlorine, iodine or fluorine. The total number of groups coordinately bonded to M is usually no greater than 6 or less than 4. These catalysts are useful for the isomerization of internal olefins to primary olefins and their subsequent hydroformylation to linear normal aldehydes. When the reactor gas is altered to essentially pure hydrogen, the catalyst further converts unsaturated organic materials to fully saturated materials under the same reaction conditions. The catalyst is oxygen stable and is easily recovered. The catalyst is well suited for continuous fixed-bed reactions.

Representative examples of heterocyclic nitrogen-containing polymers useful in the instant invention are polyvinylpyridine/divinylbenzene copolymers such as 4-vinylpyridine/divinylbenzene, 3-vinylpyridine/divinylbenzene, 2-vinylpyridine/divinylbenzene; also polyphenylquinoxaline/divinylbenzene copolymer, poly[N-vinylcarbazole]/divinylbenzene copolymer and polyvinylimidazole/divinylbenzene copolymer.

The rhodium metal catalyst described herein as polymer bound was first described as a non-bound catalyst by Abley et al in the Journal of Chemical Society (C), 840 (1971). However, this reference only discloses a hydrogenation activity for this catalyst and likewise does not show it in a bound state.

U.S. Pat. No. 3,231, 621 shows hydroformylation catalysts comprising a complex between a metal such as cobalt with carbon monoxide and nitrogen-containing ligands of a substituted pyridine nature. However, metals such as rhodium and iridium are not taught to be useful in such applications. French Pat. No. 1,530,136 shows rhodium complexes with amines as hydroformylation catalysts. However, none of these references, whether singly or in combination, teach or suggest that the catalysts of the instant invention are useful for hydroformylation and olefin isomerization reactions. Also these rhodium or iridium oxo catalysts are quite inactive when used with internal olefins.

The catalyst of the instant invention does not employ any toxic ligands, is active when used with internal olefins and is highly recoverable and air stable. The catalyst is active in isomerizing the double bonds of internal olefins to an alpha position, the subsequent hydroformylation of which yields a significant percentage of linear normal aldehydes. These catalysts are very active as hydrogenation catalysts for many classes of unsaturated organic compounds. The catalysts are also useful in hydrogenation of aldehyde hydroformylation products (also known as oxo reaction products) to the alcohol analogues of the aldehydes produced, following a simple two-step, single-reactor, single-catalyst method of olefins to alcohols. This is accomplished by simply changing the reactor gas to hydrogen after the hydroformylation has been completed, purging the system of carbon monoxide and carrying out the reaction under the hydroformylation conditions of the invention.

Concisely, the synthesis sequence consists of dissolving a rhodium or iridium trihalide in a suitable organic solvent under an inert atmosphere, stirring in solution with a heterocyclic nitrogen-containing polymer (preferably polyvinylpyridine/divinylbenzene copolymer) for a period of time suitable for binding to occur, reducing the resulting product with alkali metal borohydride, and purifying the catalyst by extraction.

It is known in the art to employ amines as ligands in homogeneous hydrogenation and hydroformylation reactions. However, such soluble catalysts generally present severe metal recovery problems, making them economically unfeasible in industrial applications. Many such soluble catalysts have been described and representative of such descriptions are German Offenlegungsschrift Nos. 1,902,560 and 2,357,645. The instant invention overcomes these limitations by complexing rhodium and iridium to an insoluble polymeric pyridine ligand support, thus allowing recovery from all reaction mixtures by simple filtration while concurrently providing a method for isomerizing internal olefins to primary olefins.

The catalysts of the instant invention can also be used as homogeneous catalysts in the hydroformylation of olefins to aldehydes. This activity of the catalysts has not been previously suggested. The catalyst of the instant invention in a homogeneous state would be a bis(-pyridine) dimethylformamide dihalo metal borohydride, wherein the metal is selected from the group consisting of rhodium and iridium. Iridium has not previously been suggested for this catalyst although it has been found to be effective in hydroformylation reactions.

Even in a homogeneous state the catalysts are recoverable by thin film distillation, especially since they are temperature and air insensitive to a large degree. However, the polymer bound version is preferred.

Although reaction temperatures are described as between 60° and 150° C., higher reaction temperatures are possible as the pressure exceeds about 2500 pounds per square inch gauge (psig). Pressures can range up to about 3500 psig limited usually only by reactor material considerations. High temperatures without sufficient pressure are not preferred.

Hydroformylation reactions are carried out in the presence of mixtures of hydrogen and carbon monoxide. The reaction requires that 1 mole of carbon monoxide be present for each mole of olefin reactant. Therefore the preferred ratio is about 1:1 hydrogen to carbon monoxide. However the ratio of hydrogen to carbon monoxide will range from about 1:100 to about 100:1 respectively although from about 80:20 to about 20:80 respectively is preferred, and from about 60:40 to about 50:50 respectively is more preferred and 50:50 respectively is most preferred.

The catalyst of the instant invention utilizes a heterocyclic nitrogen-containing polymer as a combination support and ligand for bound rhodium and iridium catalysts. The preparation of the polymer bound catalyst is simple and chemically binds the catalyst to the polymer for easy recovery and reuse.

Concisely, the rhodium or iridium catalyst is dissolved in a suitable organic solvent, a heterocyclic nitrogen-containing polymer is added, the mixture is refluxed for a sufficient period of time to bind the metal to the polymer, the resultant product solvated in DMF is reduced with sodium borohydride or other suitable reducing agents, and the catalyst is purified by extraction. At the conclusion of the preparation, the catalyst and the metal complex are chemically bound, oxygen stable, easily handled and recovered.

The polymer to which the metal is bound may require a swelling solvent for good catalyst activity depending upon the cross-linking percentage of the polymer. Highly crosslinked resins (above about 20–25% crosslinked) will not require a swelling solvent where resins with lower crosslinking will require a swelling solvent to effect the maximum efficiency of the reaction. However, if slower reaction rates are not a detriment, a solvent is not critical to the instant invention. Suitable solvents useful in the instant invention are those capable of swelling such polymers. Representative examples of such solvents are tetrahydrofuran (THF), benzene, toluene, xylenes, acetophenone, and dimethylformamide (DMF).

The invention is more concretely described with reference to the examples below wherein all parts and percentages are by weight unless otherwise specified. The examples are provided to exemplify the instant invention and not to limit it.

All olefins used in the following examples were pretreated by percolation through a 30 centimeter by 1 centimeter silica gel column. All other reagents were used as purchased. All synthetic and transfer operation were carried out under an inert atmosphere using flame dried glassware.

Example 1

A 1% divinylbenzene/4-vinylpyridine copolymer (14 grams) was added to 50 milliliters (ml) of anhydrous ethanol followed by 3.0 grams of $RhCl_3.3H_2O$. The mixture immediately turned an ochre-color, and was then stirred for 4 hours. The treated polymer was filtered and extracted for 10 hours with tetrahydrofuran (THF) after which it was dried under vacuum at 25° C. for 24 hours. Chemical analysis of the polymer catalyst by combustion analysis and X-ray fluorescence revealed 5.85% hydrogen, 5.85% nitrogen, 5% rhodium, and 6.5% chlorine by weight.

The undried treated polymer containing rhodium trichloride (15 grams) was added to 170 ml of anhydrous THF and stirred while 40 ml of 12% sodium borohydride aqueous solution was added dropwise over the course of 2 hours. Stirring was maintained for an additional 18 hours after which the polymer was filtered and washed with five 200 ml portions of distilled water and filtered. Final purification consisted of extracting the polymer with chloroform under argon for 10 hours, then drying in vacuum at 25° C. for 12 hours. The analysis performed on the treated polymer by combustion analysis, x-ray fluorescence, and standard wet methods showed 59.67% carbon, 5.65% hydrogen, 9.13% nitrogen, 7.45% oxygen, 4% rhodium, 51.% chlorine, and 0.5% boron by weight.

Example 2

This example teaches a general method for the use of the catalyst. One gram of the catalyst, as prepared in Example 1, was dissolved in 10 ml of benzene and charged into an autoclave fitted with a magnetic stirring bar together with 0.35 grams of a $C_{13}$–$C_{14}$ internal olefin mixture (thermal distribution of $C_{13}$ and $C_{14}$ olefins). The autoclave was capped, purged with a 1:1 mixture of hydrogen and carbon monoxide 4 times to 900 psig and heated quickly in less than 20 minutes to 130° C. At this temperature the 1:1 hydrogen carbon monoxide reactor gas pressure was adjusted to 950 psig. After 6.46 hours of reaction time chemical analysis by GLC of the reaction mixture indicated a 98.7% conversion of the $C_{13}$–$C_{14}$ olefins to $C_{14}$–$C_{15}$ aldehydes. Further analysis of the aldehyde product by $C_{13}$ nuclear magnetic resonance revealed 29.6% to be linear aldehydes formed from catalyst-promoted isomerization of the double bond to an alpha position and the subsequent hydroformylation of the alpha-olefins thus formed.

Example 3

The catalyst was recovered from Example 2 by filtration under an inert atmosphere and a reaction was carried out under identical conditions as Example 2 except that the olefin charge was 35 grams of Olex 13–14 olefin mixture (trademark of and sold by Universal Oil Products). After 14.8 hours of reaction time, chemical analysis by GLC of the reaction mixture indicated a 28% conversion of $C_{13}$ and $C_{14}$ olefins to $C_{14}$ and $C_{15}$ aldehydes. The aldehyde product was 27.4% linear non-branched isomers.

Example 4

The reactor and reaction mixture of Example 3 was purged 20 times to 900 psig with pure hydrogen. The reaction temperature was maintained at 130° C. and the hydrogen pressure adjusted to 950 psig. After 4 hours of reaction time, chemical analysis of the reaction mixture indicated a 100% conversion of $C_{14}$ and $C_{15}$ aldehydes to $C_{14}$ and $C_{15}$ alcohols. Olefins remaining in the mixture were completely hydrogenated to alkanes.

Example 5

The reaction was carried out under identical conditions as that described in Example 3, using catalysts recovered from Example 4 by filtration under an inert atmosphere. Reaction conditions were altered such that hydrogen was used as the reactor gas throughout the entire reaction and 35 grams of ethyl acrylate was used as the olefin charge. After 0.17 hours of reaction time, chemical analysis of the reaction mixture indicated a 100% conversion of ethyl acrylate to ethyl propionate.

Example 6

The catalyst from Example 5 was recovered by filtration under an inert atmosphere. The reaction was carried out under identical conditions as Example 5 except that 18 grams of 1,7-octadiene was employed as the olefin charge. After 0.33 hours of reaction time chemical analysis of the reaction mixture by GLC indicated a 100% conversion of 1,7-octadiene to n-octane.

Example 7

The catalyst of Example 6 was recovered from the reactor by filtration under an inert atmosphere and a reaction was carried out under identical conditions as described in Example 5 except that 35 grams of 7-tetradecene was employed as the olefin charge. After 2.28 hours of reaction time chemical analysis of the reaction mixture by GLC indicated an 82% conversion of 7-tetradecene to n-tetradecane.

Example 8

In order to quantify metal elution from the polymeric catalyst of the instant invention the products of each example were sampled and analyzed for rhodium content by X-ray fluorescence. The results, together with a summary of each example is presented in Table 1.

Table 1

| Example No. | Sequence No. | Substrate | Product | Reactor Gas | % Conversion/ Reaction Time (Hr) | Reactor Gas (Psig)/°C. | Rhodium Content (PPM) |
|---|---|---|---|---|---|---|---|
| 2 | 1 | Thermal Distribution $C_{13}$–$C_{14}$ olefin mixture | $C_{14}$–$C_{15}$ aldehydes | $H_2$/CO(1:1) | 98.7/6.46 | 950/130 | 260 |
| 3 | 2 | Olex 1314 olefin mixture | $C_{14}$–$C_{15}$ aldehydes | $H_2$/CO(1:1) | 28/14.83 | 950/130 | — |
| 4 | 3 | Example 3 | $C_{14}$–$C_{15}$ alcohols and $C_{14}$–$C_{15}$ alkanes | $H_2$ | 100/4 | 950/130 | 1.4 |
| 5 | 4 | Ethyl acrylate | Ethyl propionate | $H_2$ | 100/0.1666 | 950/130 | <0.17 |
| 6 | 5 | 1,7-octadiene | n-octane | $H_2$ | 100/0.333 | 950/130 | <0.30 |
| 7 | 6 | 7-tetradecene | 7-tetradecane | $H_2$ | 82/2.283 | 950/130 | <0.21 |

In addition to the polymer bound catalysts described and exemplified, the catalyst of the instant invention are also effective in oxo reactions in an homogeneous form as a bis pyridine dimethylformamide dihalo metal borohydride having the general structure

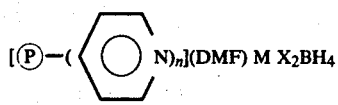

wherein M is rhodium or iridium and X is a halogen. This catalyst is exemplified in the examples below which are designed to illustrate the instant invention and not to limit it. All parts and percentages are by weight unless otherwise specified. All olefins used were pretreated by percolation through a silica gel column previously described. All other reagents were used as purchased.

Example 9

Bis(pyridine)dimethylformamidedichlororhodium borohydride prepared as described in *Journal of Chemical Society*, (C) 840, 1971, (Abley et al) in the amount of 0.3 grams was charged into an autoclave with 5 ml of dimethylformamide (DMF). 7-tetradecene (30 grams, 0.153 mole) was added, the reactor sealed, purged 3 times to 400 psig with a 1:1 hydrogen carbon monoxide gas mixture, heated quickly to 120° C. At this temperature the gas pressure was adjusted to 950 psig. After 300 minutes of reaction time analysis of the reaction mixture by GLC revealed a 67.3% conversion of olefin to aldehyde. Of this aldehyde product 17.3% was n-pentadecanol.

Example 10

Example 10 was carried out identically with Example 1 except that 35 grams (0.208 moles) of 1-dodecene was used as the olefin charged and the reaction temperature maintained at 122° C. After 287 minutes of reaction time, analysis of this reaction mixture by GLC revealed a 94.9% conversion of olefin to $C_{13}$ aldehydes.

Example 11

Example 11 was carried out identically with Example 1 except that 35 grams (0.192 moles) of 1-tridecene was used as the olefin charge and the reaction temperature was maintained at 130° C. After 225 minutes of reaction time, analysis of the reaction mixture by GLC revealed a 99% conversion of olefin to $C_{14}$ aldehydes.

Example 12

This example was carried out identically with Example 1 except that 35 grams of a $C_{13}$-$C_{14}$ thermal distribution olefin mixture was used as the olefin charge. No DMF was employed and the reaction temperature was maintained at 123° C. After 338 minutes of reaction time, analysis of the reaction mixture by GLC revealed a 97.9% conversion of the olefin to $C_{14}$ and $C_{15}$ aldehydes. Of the aldehyde product 24.5% was present as either n-tetradecanol or n-pentadecanol.

Although fresh catalyst charges were used for each of the above reactions, it is understood that the catalyst can be recovered from previous reactions by thin film distillation and reused, since the catalyst is air stable and heat stable.

Examples 9-12 are summarized in Table 2.

Table 2

| Ex. | Olefin Substrate | Product | Reaction Time Min. | % Conv. | Reaction Temp (°C.) Pressure |
|---|---|---|---|---|---|
| 9 | 7-tetradecene | $C_{15}$ aldehydes | 300 | 67.3 | 120/950 |
| 10 | 1-docene | $C_{13}$ aldehydes | 287 | 94.9 | 122/950 |
| 11 | 1-tridecene | $C_{14}$ aldehydes | 225 | 99.0 | 130/950 |
| 12 | Shell 1314 internal olefin mixture | $C_{14}$-$C_{15}$ aldehydes | 338 | 97.6 | 123/950 |

It should be noted that the polymer bound catalyst was continuously recovered throughout the series of experiments and that surprisingly high yields were obtained and the later experiments in spite of the losses normally encountered during handling and reaction including the efficiency of the instant reaction. While the recovery was carried out under an inert atmosphere, this being the preferred method, commercial operations could be carried out in an atmosphere with oxygen present, although a shorter catalyst life would be expected.

While certain embodiments and details have been shown for the purpose of illustrating this invention, it will be apparent to those skilled in this art that various changes and modifications may be made herein without departing from the spirit or scope of the invention.

I claim:

1. A method for converting olefins to aldehydes comprising converting said olefins in the presence of a catalyst of the formula

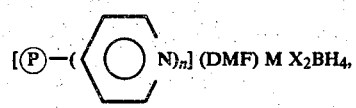

said conversions carried out at temperatures of from about 60° C. to about 150° C. and hydrogen carbon monoxide pressures of from about 300 to about 3500 psig, wherein

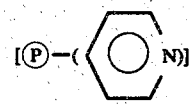

is a heterocyclic nitrogen-containing polymer is selected from the group consisting of 4-vinylpyridine/divinylbenzene, 3-vinylpyridine/divinylbenzene, 2-vinylpyridine/divinylbenzene, polyphenylquinoxaline/divinylbenzene, and poly[N-vinylcarbazole]/divinylbenzene with available pyridine linkages, M is rhodium or iridium, and X is selected from the group consisting of boron, chlorine, iodine, or fluorine and n is 1 or 2.

2. A method as described in claim 1 wherein M is rhodium.

3. A method as described in claim 2 wherein primary aldehydes are formed from internal olefins.

4. A method as described in claim 3 wherein the carbon monoxide hydrogen ratio is from about 100:1 to about 1:100 respectively.

5. A method as described in claim 4 wherein olefins formed are further converted to alcohols by purging the reactor of carbon monoxide and replacing with essentially pure hydrogen and allowing hydrogenation to occur.

6. A method as described in claim 1 wherein the total number of groups coordinately bonded to M is no greater than 6 or less than 4.

7. A method for converting olefins to aldehydes comprising converting said olefins in the presence of a catalyst at temperatures of from about 60° C. to about 150° C., wherein said catalyst is prepared by dissolving a rhodium or iridium trihalide in an organic solvent under an inert atmosphere, placing in solution with a heterocyclic nitrogen-containing polymer selected from the group consisting of 4-vinylpyridine/divinylbenzene, 3-vinylpyridine/divinylbenzene, 2-vinylpyridine/divinylbenzene, polyphenylquinoxaline/divinylbenzene, and poly[N-vinylcarbazole/divinylbenzene for sufficient time to bind the trihalide to the polymer, placing the resultant product in dimethylformamide, reducing with sodium borohydride, and extracting the catalyst prior to use.

* * * * *

UNITED STATES PATENT AND TRADEMARK OFFICE
CERTIFICATE OF CORRECTION

PATENT NO. : 4,178,312

DATED : December 11, 1979

INVENTOR(S) : John T. Carlock

It is certified that error appears in the above-identified patent and that said Letters Patent are hereby corrected as shown below:

Column 5, line 13, "20" should be --10--.

Signed and Sealed this

First Day of April 1980

[SEAL]

Attest:

SIDNEY A. DIAMOND

Attesting Officer　　　Commissioner of Patents and Trademarks